US00PP12544P2

(12) United States Plant Patent
Cosner et al.

(10) Patent No.: US PP12,544 P2
(45) Date of Patent: Apr. 16, 2002

(54) IMPATIENS PLANT NAMED 'TIPAR'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/536,166

(22) Filed: Mar. 23, 2000

(30) Foreign Application Priority Data

Mar. 30, 1999 (CA) ..... 99-1612

(51) Int. Cl.[7] ..... A01H 5/00
(52) U.S. Cl. ..... Plt./319
(58) Field of Search ..... Plt./317, 319

(56) References Cited

PUBLICATIONS

UPOV–ROM GTITM Computer Database, 2000/06, GTI Jouve Retrieval Software, citation for 'TiPar'.*

* cited by examiner

*Primary Examiner*—Bruce R. Campell
*Assistant Examiner*—Susan B. McCormick

(57) ABSTRACT

A new and distinct cultivar of *Impatiens walleriana* plant named 'TiPar', characterized by large purple bi-colored fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiPar'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The closest known cultivar of prior art is named 'Purple Star', plant patent application Ser. No. 09/078,765, which will become abandoned.

COMPARISON

The impatiens plant of the present invention differs from prior plants, namely 'Purple Star' in at least the following ways:

1. The plant of the present invention has been shown to have more light purple in the flowers in the heat than those of 'Purple Star';

2. The plant of the present invention produces more flowers in warm temperatures than 'Purple Star'; and 3. The plant of the present invention is more mounded in growth habit than the plant of 'Purple Star'.

These and other characteristics will be apparent to persons skilled in the art.

BACKGROUND—DISCOVERY

The present cultivar was developed by standard cross-polination. Its seed parent is a semi-double impatiens plant with large purple bi-colored flowers. This plant was designated B-9X-1311 under the inventors' controlled breeding program. The pollen parent is a pollen-producing double impatiens plant with purple bi-colored flowers. The plant was designated B-9X-237 under the inventors' controlled breeding program. The parent plants are not the subject of any granted patent or pending application. The cross was made in the inventors' controlled breeding program, and the first asexual reproduction was made at Coquille, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction and which are unique are the large purple bi-colored fully double flowers, flowers that are positioned above or beyond the foliage, good heat tolerance, dark green foliage and mounded, freely branching and dense plant habit, and both male and female sterility.

Color references are according to The Royal Horticultural Society Clour Chart, except where general terms of ordinary dictionary significance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching with clear water. Plants started in the last week of June and finished in late September. The light levels were between 4,000 and 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph sheet illustrates the overall appearance and the flower color of the cultivar of the present invention described herein. The photograph was taken of a mature plant 14 weeks of age during full inflorescence. There may be variations between the colors in the photograph and the colors in the following description due to light reflectance, or the amount of blue or red light captured in the film. If such variations occur, the written description shall control.

Parentage: The new cultivar was developed by standard cross-pollination. As noted above, its seed parent was a semi-double with large purple bi-colored flowers; its pollen parent was a pollen-producing double with purple bi-colored colored flowers.

Propagation:

*Type cutting.*—Lateral tips of plants were the cuttings used for asexual reproduction.

*Time to initiate roots.*—Approximately 7 to 14 days at 72° F. soil temperature.

Appearance and form of plant:

*Plant form and habit.*—Mounded with a medium vigorous, dense and bushy growing habit. A free-branching habit.

*Plant size.*—Height is about 22 cm and width is about 40 cm.

*Root description.*—The rooting habit is characterized by numerous, fibrous and well-branched roots.

*Branching habit.*—Plants are self-branching. Stems are strong and freely produced. The number of stems depends upon cultural practices, age of stems used as cuttings and the number of growth buds present on the cutting when stuck. The observed plant's average stem length is about 20 cm. Each stem generally produces about three laterals.

*Stems.*—Diameter is about 0.7 cm. Internode length is about 2 cm. Color is 146B with darker markings hard to determine, which appear close to 183B to 183C. The observed plant's stem texture is smooth.

*Foliage.*—Leaves are simple, generally symmetrical, abundant, alternate and flat. Shape is ovate wth attenuate base, acuminate apex, and crenate margin. Texture is smooth and satiny. The observed plant's leaf venation pattern is similar to other plants having similar leaf shapes, with single veins branching upwardly off from the central, longitudinal axis of each leaf, along the length of the axis, toward the margin of the leaf and forming an acute angle relative to the axis.

*Foliage size.*—Size of the largest leaves is about 7 cm in length, and 4.5 cm in width.

*Foliage color.*—Adaxial color is darker than 147A, venation color 147A; abaxial color is 147B with darker blotches close to 177A, venation color 148A.

*Petioles.*—Petiole shape is half round with a flat upper surface measuring about 3 mm wide, about 2 mm in depth, and about 2.7 cm in length. Color on the top is 148A with small hard to determine reddish streaks which appear close to 183C. Bottom color is 148A with small hard to determine reddish streaks appearing close to 183C.

*Flower size.*—Diameter of about 4 cm, and depth of about 2 cm.

*Flower texture.*—The flower texture is smooth and satiny.

*Flower count.*—Flowers per branch usually number about 15 per branch from visible buds to open flowers at a time.

*Flower fragrance.*—No discernible fragrance.

*Natural flowering season.*—Year around under greenhouse conditions, and the frost-free period from spring through fall outdoors.

*Duration of flowering.*—Continuously flowers throughout the blooming season.

*Time to flower.*—About six weeks from a rooted cutting.

*Buds.*—Ovate shape with length of about 1 cm, width of about 0.7 cm and depth of about 0.9 cm. Color of top is 144A, and bottom color is 144C.

*Petal size and shape.*—Shape is obovate to exaggerated obovate, attenuate to cunate base, entire margin, obtuse to retuse apex. Usually two petals fused at base comprise the largest petals, each being about 1.5 cm wide and 2 cm long.

*Petal color.*—Adaxial surface is variegated with, but darker than, close to 74A and 76D; abaxial surface color is variegated with 74A and 76D.

*Petal count.*—Numerous, generally 25 or more.

*Spur.*—Shape is curved acicular tapering tube with length about 2.5 cm; sepal end width about 2 mm. Color is 144B with reddish apex.

*Calyx.*—The calyx consists of a single sepal. The sepal shape is ovate with obtuse base and acute to cuminate apex, and entire margin. Length is about 1 cm and width is about 1 cm. Adaxial color is 142C with hard to determine purplish tinge appearing close to 66D; abaxial color is 142D with purplish spot that appears close to 66D.

*Peduncles.*—Length is about 2 cm and diameter is about 2 mm. Color is 146B to 146C with reddish stripes of a hard to determine color due to their small size that appears close to 172B. Peduncles have a smooth texture.

*Pedicels.*—Usually numbering 2 or 3, each having a length of about 2 cm and diameter of about 1 mm. Color is 146B to 146C with tiny hard to determine reddish stripes that appear close to 178B. Pedicles have a smooth texture.

*Reproductive organs.*—The plants of the new cultivar are both male and female sterile. No reproductive organs have been found to exist.

*Disease resistance.*—The instant plant has shown good resistance to botrytis.

*Rooting ability.*—Easy, no hormones are required.

*Cold/heat resistance.*—The instant plant produces more flowers in the heat than 'Purple Star'. In the heat, the flowers of the instant plant have more light purple than the flowers of 'Purple Star'.

What is claimed:

1. A new and distinct cultivar of *Impatiens walleriana* as illustrated and as described herein.

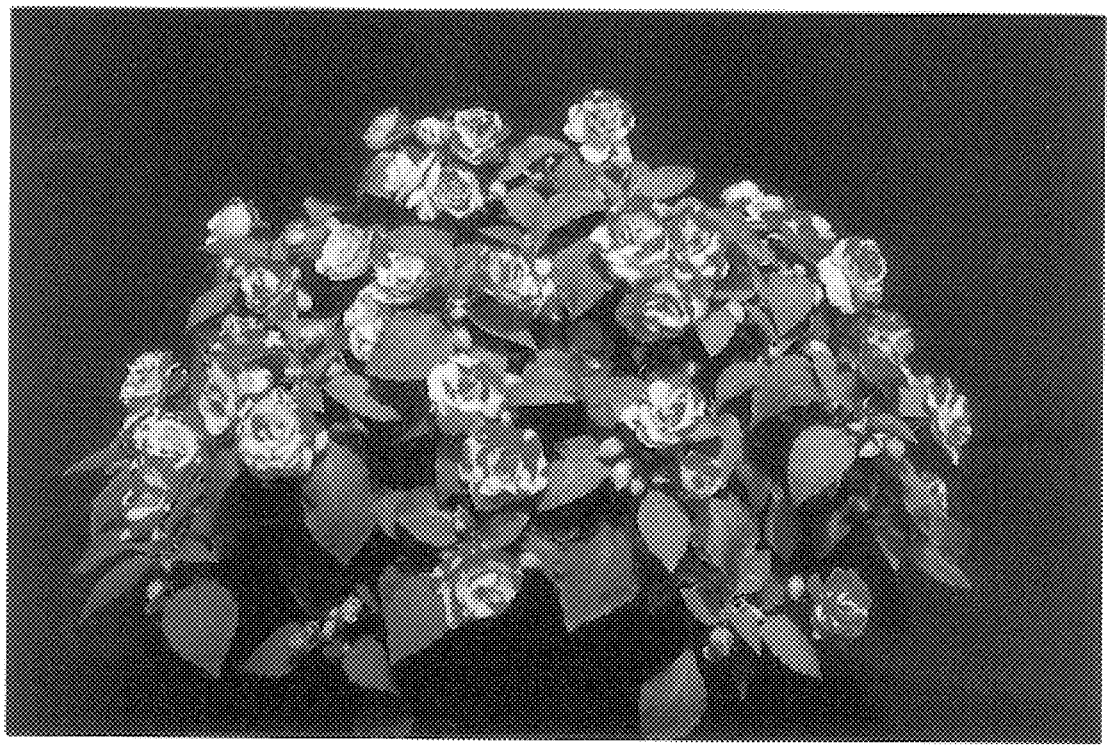

* * * * *